(12) United States Patent
Mylari et al.

(10) Patent No.: US 9,216,951 B2
(45) Date of Patent: *Dec. 22, 2015

(54) LIPID-LOWERING ANTIDIABETIC AGENT

(71) Applicant: Thetis Pharmaceuticals LLC, Southport, CT (US)

(72) Inventors: Banavara L. Mylari, Lutz, FL (US); Frank C. Sciavolino, Waterford, CT (US)

(73) Assignee: Thetis Pharmaceuticals LLC, Southport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,721

(22) Filed: Oct. 27, 2014

(65) Prior Publication Data

US 2015/0051284 A1 Feb. 19, 2015

Related U.S. Application Data

(60) Continuation of application No. 13/923,829, filed on Jun. 21, 2013, now Pat. No. 8,901,107, which is a division of application No. 13/348,265, filed on Jan. 11, 2012, now abandoned.

(60) Provisional application No. 61/461,113, filed on Jan. 12, 2011.

(51) Int. Cl.

| | | |
|---|---|---|
| A61K 31/665 | (2006.01) | |
| A61K 31/35 | (2006.01) | |
| A01N 57/00 | (2006.01) | |
| A01N 43/16 | (2006.01) | |
| C07C 279/04 | (2006.01) | |
| A61K 31/202 | (2006.01) | |
| C07C 279/26 | (2006.01) | |
| A61K 31/155 | (2006.01) | |
| C07C 57/03 | (2006.01) | |

(52) U.S. Cl.
CPC ............ *C07C 279/04* (2013.01); *A61K 31/155* (2013.01); *A61K 31/202* (2013.01); *C07C 57/03* (2013.01); *C07C 279/26* (2013.01)

(58) Field of Classification Search
CPC ........................... A61K 31/355; A61K 31/665
See application file for complete search history.

(56) References Cited

U.S. PATENT DOCUMENTS

| | | | |
|---|---|---|---|
| 5,795,909 A | 8/1998 | Shashoua et al. | |
| 6,491,950 B1 | 12/2002 | Gutierrez-Rocca et al. | |
| 6,602,902 B2 | 8/2003 | Shashoua et al. | |
| 6,667,064 B2 | 12/2003 | Surette | |
| 6,720,001 B2 | 4/2004 | Chen et al. | |
| 6,881,854 B2 | 4/2005 | Ptock et al. | |
| 6,893,627 B2 | 5/2005 | Ribnicky et al. | |
| 7,105,572 B2 | 9/2006 | Sato | |
| 7,195,914 B2 | 3/2007 | Surette | |
| 7,199,151 B2 | 4/2007 | Shashoua et al. | |
| 7,223,770 B2 | 5/2007 | Zhang et al. | |
| 7,304,089 B2 | 12/2007 | Kramer et al. | |
| 7,429,395 B2 | 9/2008 | Campbell-Tofte | |
| 7,553,870 B2 | 6/2009 | Shibuya | |
| 7,579,025 B2 | 8/2009 | Campbell-Tofte | |
| 7,619,002 B2 | 11/2009 | Shibuya | |
| 7,666,898 B2 | 2/2010 | Chang et al. | |
| 7,670,612 B2 | 3/2010 | Miller | |
| 7,973,073 B2 | 7/2011 | Mylari et al. | |
| 2003/0077335 A1 | 4/2003 | Richardson et al. | |
| 2003/0220301 A1 | 11/2003 | Lal et al. | |
| 2005/0158374 A1 | 7/2005 | Wong et al. | |
| 2005/0165102 A1 | 7/2005 | Wong et al. | |
| 2005/0182029 A1 | 8/2005 | Lal | |
| 2005/0182089 A1 | 8/2005 | Friedl et al. | |
| 2006/0159746 A1 | 7/2006 | Troup et al. | |
| 2006/0229359 A1 | 10/2006 | Zhang et al. | |
| 2006/0240095 A1 | 10/2006 | Junien et al. | |
| 2007/0207196 A1 | 9/2007 | Zhang | |
| 2007/0293562 A1 | 12/2007 | Mylari et al. | |
| 2008/0045559 A1 | 2/2008 | Zhang et al. | |
| 2008/0200533 A1 | 8/2008 | Krishnan | |
| 2008/0260819 A1 | 10/2008 | Fleming et al. | |
| 2009/0047340 A1 | 2/2009 | Guilford | |
| 2009/0054513 A1 | 2/2009 | Webster et al. | |
| 2009/0156612 A1 | 6/2009 | Kuroita et al. | |
| 2009/0227560 A1 | 9/2009 | Kuroita et al. | |
| 2010/0035990 A1 | 2/2010 | Bryhn et al. | |
| 2010/0105773 A1 | 4/2010 | Smith et al. | |
| 2010/0121048 A1 | 5/2010 | Kuroita et al. | |
| 2010/0137587 A1 | 6/2010 | Takanobu et al. | |
| 2010/0324010 A1 | 12/2010 | Imaeda et al. | |
| 2011/0046053 A1 | 2/2011 | Kidron | |
| 2011/0052678 A1 | 3/2011 | Shantha et al. | |
| 2012/0178813 A1 | 7/2012 | Mylari et al. | |
| 2013/0281535 A1 | 10/2013 | Mylari et al. | |
| 2013/0281536 A1 | 10/2013 | Pinchera et al. | |
| 2014/0100273 A1 | 4/2014 | Bobotas et al. | |
| 2014/0107360 A1 | 4/2014 | Mylari et al. | |

FOREIGN PATENT DOCUMENTS

| | | | |
|---|---|---|---|
| WO | WO-03068209 A1 | 8/2003 | |
| WO | 2004/028469 A2 | 4/2004 | |
| WO | WO-2005041923 A1 | 5/2005 | |
| WO | WO-2005042539 A1 | 5/2005 | |
| WO | WO-2005118612 A1 | 12/2005 | |
| WO | WO-2010127099 A2 | 11/2010 | |

*Primary Examiner* — Yong Chong
(74) *Attorney, Agent, or Firm* — Mintz Levin Cohn Ferris Glovsky and Popeo, P.C.; Muriel Liberto, Esq.

(57) ABSTRACT

A composition which includes a salt of metformin and the use of the composition for treatment of or use in prediabetes, diabetes, lowering triglycerides and/or other conditions in mammals.

10 Claims, No Drawings

LIPID-LOWERING ANTIDIABETIC AGENT

CROSS-REFERENCE TO RELATED APPLICATIONS

The present application is a continuation of U.S. application Ser. No. 13/923,829, filed Jun. 21, 2013, which is a divisional of U.S. application Ser. No. 13/348,265, filed Jan. 11, 2012, which claims priority from U.S. provisional patent application 61/461,113 filed on Jan. 12, 2011, the contents of which are incorporated by reference.

BACKGROUND OF THE INVENTION

1. Field of the Invention

The present invention relates to salts of poly unsaturated fatty acids with biguanides.

2. Technical Background

Diabetes mellitus has become pandemic and according to a forecast by the World Health Organization, there will be a sharp increase in the number of diabetic patients by the year 2030. This is an ominous forecast, because managing the long-term complications of diabetes, which include nephropathy, neuropathy, retinopathy, and cardiovascular complications, will have a serious impact on public health budgets. The hallmark of diabetes is chronically elevated blood glucose levels. It is also known that abnormally elevated glucose levels have an adverse impact on glutathione levels in key diabetic tissues. Furthermore, increased oxidative stress and increased production of reactive oxygen species are implicated under hyperglycemic conditions.

In spite of the early discovery of insulin and its subsequent widespread use in the treatment of diabetes, and the later discovery of and use of sulfonylureas, and thiazolidenediones, such as troglitazone, rosiglitazone or pioglitazone, as oral hypoglycemic agents, the treatment of diabetes remains less than satisfactory.

The use of insulin requires multiple daily doses, usually by self-injection. Determination of the proper dosage of insulin requires frequent estimations of the sugar in urine or blood. Treatment of non-insulin dependent diabetes mellitus (type 2 diabetes, NIDDM) usually consists of a combination of diet, exercise, oral hypoglycemic agents, e.g., thiazolidenediones, and, in more severe cases, insulin. However, the clinically available hypoglycemic agents can either have side effects limiting their use, or an agent may not be effective with a particular patient. In the case of insulin dependent diabetes mellitus (Type I), insulin administration usually constitutes the primary course of therapy.

The biguanide metformin is a known compound approved by the U.S. Food & Drug Administration for the therapeutic treatment of diabetes. The compound and its preparation and use are disclosed, for example, in U.S. Pat. No. 3,174,901. Metformin is orally effective in the treatment of type 2 diabetes. Metformin (N,N-dimethylimidodicarbonimidic diamide) is a biguanide, anti-hyperglycemic agent currently marketed in the United States in the form of its hydrochloride salt 1,1-dimethylbiguanide hydrochloride (Formula 1a).

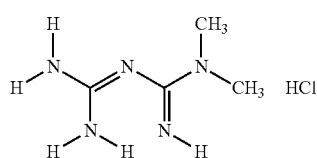

Formula 1a

Metformin hydrochloride can be purchased commercially and can also be prepared, for example, as disclosed in J. Chem. Soc., 1922, 121, 1790.

U.S. Pat. No. 7,973,073 B2 (Mylari) describes use of metformin R-(+) lipoate as being useful for treating diabetes or diabetic complications.

U.S. Patent Publication 2005/0165102 describes complexes of drugs (metformin being mentioned) with transport moieties (fatty acids being mentioned) to enhance absorption and control delivery of the drugs being used. Among the fatty acid complexing agents mentioned are caprate, laurate, palmitate and oleate.

U.S. Patent Publication 2005/0182029 describes metformin salts of lipophilic acid salts (fatty acids being mentioned), their pharmaceutical formulations, and methods of administering the metformin salts for the treatment of hyperglycemia.

According to United Kingdom Perspective Diabetes Study (UKPDS) (Clarke et al. Diabetologia, 2005, 48, 868-877), metformin therapy was cost-saving and increased quality-adjusted life expectancy. In the UKPDS, overweight and obese patients randomized to initial therapy with metformin experienced significant reductions in myocardial infarction and diabetes-related deaths. Metformin does not promote weight gain and has beneficial effects on several cardiovascular risk factors. Accordingly, metformin is widely regarded as the drug of choice for most patients with Type 2 diabetes.

Prediabetes is a syndrome. Many patients with type 2 diabetes and with a prediabetic condition known as metabolic syndrome suffer from a variety of lipid disorders including elevated triglycerides. The body uses triglycerides to store fat but high (>200 mg/dl) and very high (>500 mg/dl) triglycerides are associated with atherosclerosis which increases the patients risk of heart attack and stroke.

Incipient diabetes with impaired glucose tolerance is another prediabetic condition. Overall, type 2 diabetes and incipient diabetes with impaired glucose tolerance, are intimately intertwined with obesity, hyperlipidemia, including hypertriglyceridemia, and cardiovascular complications including arrhythmia, cardiomyopathy, myocardial infarction, stroke and heart failure. Clinically, pre-diabetes means that blood sugar level is higher than normal, but it's not yet increased enough to be classified as type 2 diabetes. Still, without intervention, prediabetes is likely to become type 2 diabetes over time Also diabetic patients have impaired circulation which manifests itself in the slow healing of wounds in the foot and lower leg and puts the patient at risk for amputation.

Elevated triglycerides may be lowered by diet and exercise. Niacin and omega-3 fatty acids, commonly known as fish oil, are frequently used in the management of hypertriglyceridemia. Omega-3 fatty acids are unsaturated carboxylic acids which have a terminal double bond three carbons from the methyl terminus, the 3 position. Omega-3 fatty acids are commonly extracted from oily fish like salmon, mackerel and menhaden. They are also extracted from other marine sources like squid and krill. Omega-3 fatty acids are commercially available. The omega-3 fatty acids most commonly extracted from fish are eicosapentaenoic acid and docosahexaenoic acid. These compounds have been shown to have beneficial effects in treating obesity, arrhythmia, and myocardial infarction and have the structures:

Structure 1

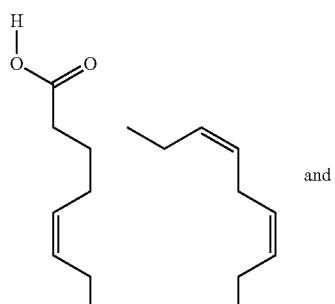

eicosapentaenoic acid

Structure II

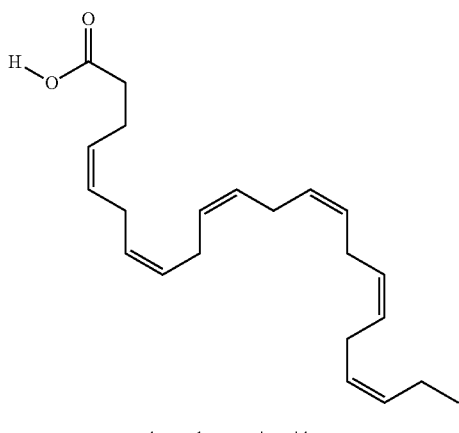

docosahexaenoic acid:

Resolvins are a special class of polyhydroxylated omega-3 fatty acids which possess potent antiinflammatory and immunoregulatory actions. These biological actions of resolvins are thought to play a significant role in cardiovascular and diabetic conditions.

SUMMARY OF THE INVENTION

This present invention provides compositions of the formula I:

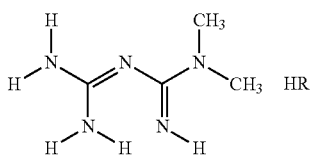

Wherein HR is an omega-3 polyunsaturated $C_{16-24}$ fatty acid optionally substituted with from 1-3 hydroxy groups.

The compositions are typically compounds in the form of salts of metformin and an omega-3 polyunsaturated fatty acid (RH) in which the biguanide moiety is protonated and the acid moiety is at least partially in ionic form. In some instances, however, for example depending on the pH of the environment, the composition may be in the form of a mixture of the biguanide and acid components. The invention also provides pharmaceutical compositions comprising compositions of formula I and pharmaceutically acceptable excipients. The invention further provides methods for treating diabetes (especially type 2 diabetes), obesity, cardiac arrhythmia, myocardial infarction and elevated triglycerides. The compounds and compositions of this invention may provide high blood levels of the compositions of structure 1, when administered to patients, preferably by oral administration.

Particularly useful compounds are those wherein HR is a fatty acid of 20 or 22 carbon atoms with four or five unsaturated bonds in addition to the required omega-3 unsaturated bond such as 4,7,10,13,16, 19 docoshexaenoic acid, 5, 8, 11, 14 eicosopentanoic acid and resolvins derived from these acids such as the 5, 12, 18 trihydroxy eicosopentanoic acid known as resolvin E1, the 15, 18 dihydroxy eicosopentanoic acid, known as resolvin E2, the 7, 8, 17 trihydroxy docosahexaenoic acid known as resolvin D1, and its 7,16, 17 trihydroxy eipmer known as resolvin D2, the 4,11,17 trihydroxy docosahexaenoic acid known as resolvin D3 and the 4,5, 17 trihydroxy docosahexaenoic acid known as resolvin D4.

The invention relates to a compound of formula I which is a salt of metformin and an omega-3 polyunsaturated fatty acid and is meant to include any polymorphs, solvates, and hydrates thereof.

In one preferred embodiment, RH is a resolving. In the most preferred embodiment, RH is eicosapentaenoic acid or docosahexaenoic acid.

Compounds of the present invention can be considered as designer dual-acting drugs and additionally possess a means for improving the bioavailability of their component moieties as a result of their high degree of water solubility.

In certain embodiments, the invention relates to a mixture of metformin or a pharmaceutically acceptable salt thereof, (e.g., hydrochloride, succinate, fumarate) with an omega-3 polyunsaturated fatty acid (RH), or a pharmaceutically acceptable salt thereof. In one preferred embodiment, RH is a resolvin. In the most preferred embodiment, RH is eicosapentaenoic acid or docosahexaenoic acid.

The present invention provides a pharmaceutical composition of the invention comprising compound of formula I and a pharmaceutically-acceptable carrier, vehicle or diluent.

The pharmaceutical composition may, for example, be in a form suitable for oral administration as a tablet, capsule, pill, powder, sustained release formulation, solution, suspension, for parenteral injection as a sterile solution, suspension or emulsion. Such compositions and methods for their preparation may be found, for example, in 'Remington's Pharmaceutical Sciences', 19th Edition (Mack Publishing Company, 1995). The pharmaceutical composition may be in unit dosage forms suitable for single administration of precise dosages. The pharmaceutical composition will include a conventional pharmaceutical carrier or excipient and an active compound.

Formulations suitable for oral administration include solid formulations such as tablets, capsules containing particulates, liquids, or powders, lozenges (including liquid-filled lozenges), chews, multi- and nano-particulates, gels, solid solution, liposome, films, ovules, sprays and liquid formulations.

Tablet dosage forms typically also include a disintegrant (such as sodium starch glycolate, sodium carboxymethyl cellulose, calcium carboxymethyl cellulose, polyvinylpyrrolidone, methyl cellulose, microcrystalline cellulose, lower alkyl-substituted hydroxypropyl cellulose, starch, pregelatinised starch and sodium alginate) a binder (such as microcrystalline cellulose, gelatin, a sugar, polyethylene glycol, natural and synthetic gums, polyvinylpyrrolidone, pregelatinised starch, hydroxypropyl cellulose and hydroxypropyl methylcellulose) and a lubricant (such as magnesium stearate, calcium stearate, zinc stearate, sodium stearyl fumarate, and mixtures of magnesium stearate with sodium lauryl sulfate). A diluent such as lactose, mannitol, xylitol, dextrose, sucrose, sorbitol, microcrystalline cellulose, starch and dibasic calcium phosphate dehydrate) may also be present. Compositions of the invention may also be administered for example as capsules made, for example, from gelatin or hydroxypropylmethylcellulose.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, Liquid formulations may also be prepared by the reconstitution of a solid, for example, from a sachet. The compositions of the invention may also be used in fast-dissolving, fast-disintegrating dosage forms such as those described in Expert Opinion in Therapeutic Patents, 11 (6), 981-986, by Liang and Chen (2001).

Other formulations will be apparent to those skilled in the art.

The invention further provides methods for treatment or lowering the risk of developing conditions such as diabetes, especially type 2 diabetes, prediabetes, obesity, arrhythmia, myocardial infarction and stroke by administering therapeutically effective amounts of compositions of formula I. Such compositions may also be used to lower triglyceride levels in a subject and so have a role in treatment of diabetes exacerbated with high triglyceride levels. Suitable dosages may be determined by conventional means.

The triglyceride lowering efficacy of the compounds of the present invention can be determined in animal models according to the procedure described by Sidika et al in Journal of Lipid Research, 1992, 33, 1-7.

The following example describes a diabetic rat model that may be used for determination of conditions leading to a method for treatment and prevention of post-ischemic damage of the heart and heart tissue.

Spontaneously diabetic Bio-Bred (BB/W) rats from the colony maintained at the University of Massachusetts Medical Center, Worcester, were used in this study. BB/W rats were chosen for the current study because the BB/W rats have been considered a useful model of autoimmune human insulin-dependent diabetes DM). Like human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves have all been well documented in BB rats, as described in *Diab. Metab. Rev.*, 8:9 (1992). The BB/W rats were 3 to 4 months old and weighed about 300 to 350 g. The BB/W rats received daily insulin, which was discontinued 24 h prior to performing the isolated heart perfusion studies, leading to a hyperglycemic state. The rats were acutely diabetic, receiving 2.02±0.04 units of insulin daily, and had been diabetic for at least 12±3 days. The mean blood glucose levels in these diabetic rats were 386±24 mg/dL. The age-matched non-diabetic controls had mean blood glucose levels of 92±12 mg/dL.

Isolated Perfused Heart Model

This example describes an isolated perfused rat heart model used in development of the invention. Studies are performed using an isovolumic isolated rat heart preparation. Acutely diabetic male BB/W rats and non-diabetic age-matched (3 to 4 months old) control are pretreated with heparin (1000 u; IP), followed by sodium pentobarbital (65 mg/kg; IP). After deep anaesthesia is achieved as determined by the absence of a foot reflex, the hearts are rapidly excised and placed into iced saline. The arrested hearts are retrograde perfused in a non-recirculating model through the aorta within 2 minutes following their excision. Left ventricular developed pressure (LVDP) is determined using a latex balloon in the left ventricle with high pressure tubing connected to a pressure transducer. Perfusion pressure is monitored using high pressure tubing off the perfusion line. Hemodynamic measurements are recorded on a 4-channel Gould recorder. The system has two parallel perfusion lines with separate oxygenators, pumps and bubble traps, but common temperature control allows rapid change perfusion media. The hearts are perfused using an accurate roller pump. The perfusate consists of 118 mM NaCl, 0.47 mM KCl, 12 mM $CaCl_2$, 12 mM MgCl2, 25 mM $NaHCO_3$, and the substrate 11 mM glucose. The perfusion apparatus is tightly temperature-controlled, with heated baths being used for the perfusate and for the water jacketing around the perfusion tubing to maintain heart temperature at 37±0.5° C. under all conditions. The oxygenated perfusate in the room temperature reservoir is passed through 25 ft. of thin-walled silicone tubing surrounded by distilled water at 37° C. saturated with 95% oxygen. The perfusate then enters the water-jacketed (37° C.) tubing leading to the heart through a water jacketed bubble trap. This preparation provides excellent oxygenation that routinely has been stable for 3 to 4 hours.

Model for Zero-/Low Ischemia

This example describes a procedure used for study of zero-flow ischemia in diabetic control, diabetic treated, non-diabetic treated and control isolated hearts. Diabetic control (DC) diabetic treated (DZ) normal (C) control and normal treated (CZ) hearts are subjected to 20 minutes of normoxic perfusion followed by 20 minutes of zero-flow ischemia where the perfusate flow is completely shut off, followed by 60 minutes of reperfusion. Hearts are treated with 10 μM metformin eicosapentaenoate. In the metformin eicosapentaenoate treated diabetic group (DZ), hearts are subjected to 10 minutes of normoxic perfusion with normal Krebs-Henseleit buffer and 10 minutes of normoxic perfusion with Krebs-Henseleit buffer containing 10 μM metformin eicosapentaenoate. The hearts are then subjected to 20 minutes of zero-flow ischemia followed by 60 minutes of reperfusion. In order to avoid any variability in reperfusion conditions, both DC and DZ hearts are reperfused with normal Krebs-Henseleit buffer.

Model for Low-flow Ischemia

This example describes a procedure used for study of low-flow ischemia in diabetic controls, diabetic treated, non-diabetic treated and non-diabetic control isolated hearts. Diabetic control hearts (DC) are subjected to 20 minutes of normoxic perfusion at a flow rate of 12.5 mL/minute followed by 30 minutes of low-flow ischemia where the perfusate flow is slowed down to 1.25 mL/min, that is about 10% of normal perfusion, followed by 30 minutes of reperfusion at a normal flow rate (12.5 mL/min). In the metformin eicosapentaenoate treated diabetic or non-diabetic groups (DZ or CZ), hearts are subjected to 10 minutes of normoxic perfusion (flow rate 12.5 mL/min) with normal Krebs-Henseleit buffer and 10 minutes of normoxic perfusion with Krebs-Henseleit buffer containing 10 μM metformin eicosapentaenoate. The hearts are subjected to 30 minutes of low-flow ischemia (flow rate 1.25 mL/min) and 30 minutes of reperfusion at normal flow rate (12.5 mL/min).

Animal models to determine the effects of compounds of the invention on diabetes and complications of diabetes have been reviewed by Tirabassi et al., *ILAR Journal*, 2004, 45, 292-302. Antidiabetic activity may also be tested according to protocols described in the following patents: U.S. Pat. Nos. 4,340,605; 4,342,771; 4,367,234; 4,617,312; 4687,777 and 4,703,052. Additional references relevant to this application include the following: French Patent 2796551 and United States Published Patent Application No. 20030220301.

The present invention is exemplified by the following non-limiting examples.

EXAMPLE 1

Preparation of [amino(imino)methyl]amino}(dimethylamino)methaniminium (5Z,8Z,11Z,14Z,17Z)-eicosa-5,8,11,14,17-pentaenoate) delete N,N-dimethylimidodicarbonimidic diamide. N,N-dimethylimidodicarbonimidic diamide hydrochloride (4.01 g, 24.3 mmol) was dissolved in 1N sodium hydroxide (24.2 mL, 24.2 mmol) and stirred at room temperature for 30 minutes. The solution was concentrated in vacuo and to the residue was added ethanol (80 mL). The mixture was carefully concentrated to azeotropically remove water. To the resulting solid was added EtOH (60 mL) and the suspension was filtered to remove precipitated NaCl. The filtrate was concentrated and the resulting solid was placed on high vacuum overnight to yield 3.18 g (102%) of metformin as a white solid.

{[Amino(imino)methyl]amino}(dimethylamino)methaniminium (5Z,8Z,11Z,14Z,17Z)-eicosa-5,8,11,14,17-pentaenoate Metformin free base (2.67 g, 20.7 mmol) was dissolved in acetonitrile (100 mL) and the resulting solution was filtered through a medium frit to remove a small amount of NaCl that precipitated. To the filtrate was added dropwise at room temperature (over a 5 minute period) a solution of (5Z,8Z,11Z,14Z,17Z)-eicosa-5,8,11,14,17-pentaenoic acid (5.40 g, 17.8 mmol) in acetonitrile (30 mL). A white solid precipitated immediately upon addition of the acid. The reaction flask was covered in foil to protect it from light. The mixture was stirred for one hour at room temperature and was then chilled to 0° C. for 1 hour, and then filtered under an atmosphere of nitrogen. The resulting solid was washed with 50 mL acetonitrile and then quickly transferred to a foil-covered round bottom flask and placed under high vacuum. The material was left under high vacuum overnight to yield 6.5 (84%) of the title compound of Example 1 as a light tan solid; MP 121-124° C. (with decomposition); $^1$H NMR (400 MHz, MeOD) d 5.36 (m, 10H), 3.03 (s, 6H), 2.84 (m, 8H), 2.18 (m, 2H), 2.10 (m, 4H), 1.66 (in, 2H), 0.97 (t, J=7.57 Hz, 3H); MS (ESI−) for $C_{20}H_{24}O_2$ m/z 301.2 (M-H).

EXAMPLE 2

Preparation of {[amino(imino)methyl]amino}(dimethylamino)methaniminium (4Z,7Z,10Z,13Z,16Z,19Z)-docosa-4,7,10,13,16,19-hexaenoate N,N-dimethylimidodicarbonimidic diamide. N,N-dimethylimidodicarbonimidic diamide hydrochloride (4.06 g, 24.5 mmol) was dissolved in 1N sodium hydroxide (24.5 mL, 24.5 mmol) and stirred at room temperature for 30 minutes. The solution was concentrated in vacuum and to the residue was added ethanol (80 mL). The mixture was carefully concentrated to azeotropically remove water. To the resulting solid was added (60 mL) and the suspension was filtered to remove precipitated sodium chloride. The filtrate was concentrated and the resulting solid was placed on high vaccum overnight to yield 3.22 g (102%) of N,N-dimethylimidodicarbonimidic diamide as a white solid.

{[Amino(imino)methyl]amino}(dimethylamino)methaniminium (4Z,7Z,10Z,13Z,16Z,19Z)-docosa-4,7,10,13,16,19-hexaenoate.

N,N-Dimethylimidodicarbonimidic diamide (968 mg, 7.61 mmol) was dissolved in acetonitrile (36 mL) and the resulting solution was filtered through a medium frit to remove a small amount of sodium chloride that precipitated. To the filtrate was added dropwise at room temperature (over a 5 minute period) a solution of (4Z,7Z,10Z,13Z,16Z,19Z)-docosa-4,7,10,13,16,19-hexaenoic acid (2.00 g, 6.09 mmol) in acetonitrile (35 mL). A white solid precipitated immediately upon addition of the acid. The reaction flask was covered in foil to protect it from light. After stirring for 1 h at room temperature, the mixture was chilled to 0° C. for 1 h, and then filtered under an atmosphere of nitrogen. The solid was washed with 50 mL ice-cold acetonitrile and then quickly transferred to a foil-covered round bottom flask and placed under high vac. The material was left under high vacuum overnight to yield 2.54 g (91%) of 1 as a light tan solid. The material was found to be air and light sensitive, and was therefore stored in an amber vial under nitrogen: MP 124-127° C. (turned brown); $^1$H NMR (400 MHz, MeOD) 5.36 (m, 12H), 3.03 (s, 6H), 2.85 (m, 10H), 2.37 (m, 2H), 2.19 (m, 2H), 2.09 (m, 2H), 0.97 (t, J=7.57 Hz, 3H); MS (ESI−) for $C_{22}H_{32}O_2$ m/z 327.3 (M-H).

EXAMPLE 3

Preparation of {[amino(imino)methyl]amino}(dimethylamino)methaniminium (5Z,8Z,11Z,14Z,17Z)-eicosa-5,8,11,14,17-pentaenoate N,N-dimethylimidodicarbonimidic diamide Metformin hydrochloride (331.25 g, 2 moles) was weighed into a 4000 mL beaker containing a stir bar. 1N KOH (1980 mL, 1.998 moles) was added, the beaker was covered, and the mixture was stirred for 2 h. The solids were collected by vacuum filtration, and the filtrate was concentrated to a damp solid. Isopropanol (500 mL) was added and after brief swirling, the mixture was concentrated. The residual white solid was dried for 16 h in a vacuum oven (yield: 269.08 g).

{[Amino(imino)methyl]amino}(dimethylamino)methaniminium (5Z,8Z,11Z,14Z,17Z)-eicosa-5,8,11,14,17-pentaenoate Metformin free base (50.10 g, 0.366 mole) was weighed into a 4000 mL beaker containing a stir bar. $CH_3CN$ (2000 mL) was added and the mixture was rapidly stirred until all metformin had dissolved. A fine white solid was removed by vacuum filtration. After ~30 min, the hazy filtrate was vacuum filtered through the same medium, and the clear filtrate was transferred to a 5000 mL 3-necked round bottom flask, which was fitted with a complete stir shaft assembly, $N_2$ inlet and addition funnel and bubbler. The funnel was charged with a solution of eicosapentaenoic acid (100.01 g, 0.324 mole) in acetonitrile (500 mL) which was added drop-wise over 70 min. After stirring for 2 h, the flask was fitted with a $N_2$ balloon, sealed, and placed in the refrigerator over-night. The off-white solid was collected by vacuum filtration and washed with acetonitrile (500 mL). The damp solid was transferred to a pyrex dish, which was stored in a vacuum oven for 24 h. The oven was vented with nitrogen gas, and the beige solid was coarsely ground in a mortar with pestle then transferred to an amber jar that had been flushed with $N_2$ to obtain the compound of Example 3 (yield: 130.49 g).

EXAMPLE 4

The solubility of the compound of Example 1 in water was compared with that of eicosapentaenoic acid (EPA).

Measurement of the water solubility of the test compounds is accomplished by using methods well known to those skilled in the art. Specifically, to a weighed amount of the test compound of Example 1 distilled water is added in small portions until a clear solution is obtained. The total volume of the solution is measured. The water solubility is calculated by dividing the weight of the salt, in mg, by the volume of the solution, in mL. The water solubility of the compound of Example 1 when measured using the above technique, was determined to be 50 mg/ml. Likewise, the water solubility of EPA was found to be <0.2 mg/mL. The compound of Example 1 is therefore, at least, 250 times more soluble in water than EPA itself. This is a clear indication of an unexpectedly high degree of bioavailability of the compositions of the invention. Highly water soluble medicinal preparations, when administered orally, result in efficient absorption of such preparations from the gastrointestinal tract into systemic circulation. Such preparations permit rapid absorption into the blood stream resulting in a high concentration of the active agent in the blood. Furthermore, water soluble preparations are especially suitable for parenteral administration, for example, intravenous administration.

What is claimed is:

1. A method of treating a prediabetic condition in a subject in need thereof, the method comprising administering to the subject a therapeutically effective amount of a pharmaceutical composition comprising a metformin salt of a polyunsaturated fatty acid selected from eicosapentaenoic acid (EPA), docosahexaenoic acid (DHA), and mixtures thereof.

2. The method of claim 1, wherein the pharmaceutical composition has an aqueous solubility of at least 50 mg/ml under standard conditions.

3. The method of claim 1, wherein the subject has serum triglyceride levels of greater than 200 mg/dl.

4. The method of claim 1, wherein the subject has hypertriglyceridemia.

5. The method of claim 1, wherein the metformin salt of a polyunsaturated fatty acid is a polymorph, solvate, or hydrate.

6. The method of claim 1, wherein the subject is further selected from the group consisting of subjects having or at risk of developing diabetes, a prediabetic condition, obesity, cardiac arrhythmia, myocardial infarction, and stroke due to high serum triglyceride levels.

7. The method of claim 1, wherein the prediabetic condition is incipient diabetes with impaired glucose tolerance.

8. The method of claim 1, wherein the polyunsaturated fatty acid is eicosapentaenoic acid (EPA).

9. The method of claim 1, wherein the polyunsaturated fatty acid is docosahexaenoic acid (DHA).

10. The method of claim 1, wherein the polyunsaturated fatty acid is a mixture of EPA and DHA.

* * * * *